(12) United States Patent
Dulgar-Tulloch et al.

(10) Patent No.: US 8,647,829 B2
(45) Date of Patent: Feb. 11, 2014

(54) SWITCHABLE AFFINITY BINDERS

(75) Inventors: Aaron Dulgar-Tulloch, Clifton Park, NY (US); Ernest William Kovacs, Albany, NY (US); Evelina Roxana Loghin, Rexford, NY (US); Anup Sood, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 969 days.

(21) Appl. No.: 12/498,485

(22) Filed: Jul. 7, 2009

(65) Prior Publication Data

US 2010/0216159 A1     Aug. 26, 2010

Related U.S. Application Data

(60) Provisional application No. 61/153,990, filed on Feb. 20, 2009.

(51) Int. Cl.
*G01N 33/53* (2006.01)
*G01N 31/00* (2006.01)

(52) U.S. Cl.
USPC ............. 435/7.21; 435/7.1; 436/86; 436/501; 436/518; 514/23; 514/80; 514/424; 514/532; 530/300; 530/350

(58) Field of Classification Search
None
See application file for complete search history.

(56) References Cited

U.S. PATENT DOCUMENTS

| | | | |
|---|---|---|---|
| 5,985,658 | A | 11/1999 | Colinas et al. |
| 6,087,330 | A | 7/2000 | Kogan et al. |
| 2005/0054000 | A1 | 3/2005 | Dubel |
| 2007/0202530 | A1 | 8/2007 | Ross et al. |

FOREIGN PATENT DOCUMENTS

| | | |
|---|---|---|
| WO | 0153325 A2 | 7/2001 |
| WO | 2007046825 A2 | 4/2007 |
| WO | 2008070816 A2 | 6/2008 |

OTHER PUBLICATIONS

Megeed et. al. (Biomacromolecules, Apr. 2006, vol. 7, No. 4, pp. 999-1004).*
Chockalingam et al. (Protein Engineering Design and Selection, pp. 1-7, 2007).*
PCT/EP2010/051967 Search Report and Written Opinion, Nov. 1, 2010.
M. Zheng et al., "Redox Sensing by Prokaryotic Transcription Factors," Biochemical Pharmacology, vol. 59, 2002, pp. 1-6.
M.B. Tolendano et al., "Redox-Dependent Shift of OxyR-DNA Contacts along an Extended DNA-Binding Site: A Mechanism for Differential Promoter Selection," Cell Press, vol. 78, Sep. 9, 1994, pp. 887-909.
P.M. Kern et al., "UVB-irradiated T-cells undergoing apoptosis lose L-selectin by metalloprotease-mediated shedding," International Journal of Radiation Biology, vol. 76, No. 9, Feb. 10, 2000, pp. 1265-1271.
Megeed et al., "Modulation of Single-Chain Antibody Affinity with Temperature-Responsive Elastin-Like Polypeptide Linkers", Apr. 2006, vol. 7, No. 4, pp. 999-1004pp.
Mayer et al. "Biologically Active Molecules with a 'Light Switch'", Angew Chem. Inst. Ed. 2006, 45, pp. 4900-4921.
Hey et al., "Artificial, Non-abtibody Binding Proteins for Pharmaceutical and Industrial Applications", Trends in Biotechnology, vol. 23, No. 10, Oct. 2005, pp. 514-522.
Chockalingam et al. "Design and Application of Stimulus-responsive Peptide Systems", Protein Engineering, Design and Selection, pp. 1-7, 2007.
Cerasoli et al., "ZiCo: A Peptide Designed to Switch Folded State Upon Binding Zinc", J. Am. Chem. Soc., 2005, 15008-15009.
M. Aizawa et al.,"Light-Induced Enzyme Activity Changes Associated with the Photoisomerization of Bound Spiropyran," Archives of Biochemistry and Biophysics, vol. 182, pp. 305-310, 1977.

* cited by examiner

Primary Examiner — Lisa Cook
(74) Attorney, Agent, or Firm — Jenifer Haeckl

(57) ABSTRACT

Methods and kits for binding and releasing biological targets, comprising, a binder comprising an environmentally reactive molecular switch that can switch between a high affinity state, to bind the target, to a low affinity state, to release the target.

8 Claims, 8 Drawing Sheets

US 8,647,829 B2

SWITCHABLE AFFINITY BINDERS

CROSS REFERENCE TO RELATED APPLICATIONS

This application is a continuation-in-part of U.S. Provisional Patent Application No. 61/153,990, entitled "Switchable Affinity Binders", filed Feb. 20, 2009, which is herein incorporated by reference.

SEQUENCE LISTING

The instant application contains a Sequence Listing which has been submitted in ASCII format via EFS-Web and is hereby incorporated by reference in its entirety. Said ASCII copy, created on May 7, 2012, is named 2377612.txt and is 8,577 bytes in size.

BACKGROUND

The invention relates generally to affinity binders (e.g. antibodies, peptides, etc) that undergo a change in affinity upon exposure to environmental cues.

As the state of biological research, technologies, and medicine advances, there is an increasing need for improved compositions and methods to probe and/or manipulate biological manner in a gentle, non-biasing fashion. For example, the emerging field of cell therapy will soon require the ability to positively identify, purify, and administrate desired cells in a manner that leaves them unmodified and unactivated to minimize the risk of complications or non-efficacious treatment. Strategies to assist in this identification and purification typically rely on specific, high affinity antibodies. DETACHa-Beads (Dynal/Invitrogen), for example, are a commercially available product that captures B and T cells onto antibody-coated magnetic beads. To assist in administration, cell release is then achieved through input of a second antibody that competitively binds to the first antibody and releases cells. Another product, the Isolex Magnetic Cell Selection System (Baxter) relies on a similar approach to capture CD34+ stem cells onto magnetic beads. Cell liberation in this instance, however, occurs with the addition of a release peptide that competitively binds to a bead-bound secondary antibody. Despite the proven utility of these systems, the necessity to add additional reagents increases time, cost and has the potential to contaminate cell product with the added antibody or peptides.

Similarly, in the screening of biological samples for disease diagnosis and treatment determination, as well as in sensors for biological or defense applications, target identification is limited by the use of classical high-affinity binders, such as antibodies, which are difficult to remove without damaging the samples and reducing or eliminating the ability for further analysis. Due to these limitations, there remains a strong impetus to develop a next generation platform for biological identification and manipulation that retains the functional superiority of specific, high affinity target binding, but which enables target release upon command in a manner that leaves the biological sample intact and unmodified.

BRIEF DESCRIPTION

The invention relates to affinity binders (e.g. antibodies, peptides, etc) that undergo a significant change in affinity upon exposure to specific environmental cues. Under one environmental state, these binders demonstrate high affinity, high selectivity binding of a desired target, while in a second state they exhibit low affinity and minimal binding to the same target. These switchable affinity binders improve significantly upon classical affinity binders by offering controlled attachment and release from the target while retaining the advantages of high affinity, high selectivity binder-target interaction.

An embodiment of a kit of the invention for binding and releasing cells, comprises, a binder comprising an environmentally reactive molecular switch that can switch between a high affinity state, to bind the cells, to a low affinity state, to release the cells; wherein the binder comprises one or more of an affibody, antibody, peptide, fragments thereof, or combinations thereof.

An embodiment of a kit of the invention for binding and releasing a target, comprises, a binder comprising an environmentally reactive molecular switch that can switch between a high affinity state, to bind the target, to a low affinity state, to release the target; wherein the binder comprises a 2-helix binder. The target may comprise cells, pathogens, viruses, antibodies or antibody fragments, proteins, nucleic acids, peptides, lipids, polysaccharides, or combinations thereof.

Another embodiment of the kit of the invention for binding and releasing a target, comprises, a binder comprising an environmentally reactive molecular switch that can switch between a high affinity state, to bind the target, to a low affinity state, to release the target; wherein the binder comprises a chemically modified antibody or a fragment thereof. The target may be selected from cells, pathogens, viruses, antibodies or antibody fragments, proteins, nucleic acids, peptides, lipids, polysaccharides, or combinations thereof.

An example of the method of the invention for binding and releasing cells, comprises the steps of: contacting one or more binders to the cells, wherein the binder comprises an environmentally-reactive molecular switch that can switch between a high affinity state, to bind the cells, to a low affinity state, to release the cells; introducing a trigger for the switch to either cause the cells to bind to, or be released from, the binder. The trigger may comprise one or more of an acid, base, heat, light, magnetic field, electric field, a reducing agent, a salt or a combination thereof. The binder may comprise one or more of an affibody, antibody, peptide, fragments thereof, or combinations thereof.

An example of the method of the invention for binding and releasing a target, comprises the steps of: contacting one or more binders to the target, wherein the binder comprises an environmentally-reactive molecular switch that can switch between a high affinity state, to bind the target, to a low affinity state, to release the target, wherein the binder comprises a 2-helix binder; and initiating a trigger for the switch to either cause the target to bind to, or be released from, the binder. The target may be selected from cells, pathogens, viruses, antibodies or antibody fragments, proteins, nucleic acids, peptides, lipids, polysaccharides, or combinations thereof. The trigger may comprise one or more of an acid, base, heat, light, magnetic field, electric field, a reducing agent, a salt or a combination thereof.

Another example of the method of the invention for binding and releasing a target, comprises the steps of: contacting one or more binders to the target, wherein the binder comprises an environmentally-reactive molecular switch that can switch between a high affinity state, to bind the target, to a low affinity state, to release the target, wherein the binder comprises a chemically modified antibody or a fragment thereof; initiating a trigger for the switch to either cause the target to bind to, or be released from, the binder. The target may be selected from a cell, a pathogen, a virus, an antibody or antibody fragment, a protein and a nucleic acid. The trigger comprises one or more of an acid, base, heat, light, a reducing agent, a salt or a combination thereof.

An example of the method of the invention for detecting multiple targets in a sample comprises the steps of, applying a probe, comprising a binder comprising an environmentally reactive molecular switch that can switch between differing affinity states, to a sample to bind a target of interest; detecting the probe; applying an external stimulus to release the probe from the target of interest; applying a second probe to bind a second target of interest; detecting the second probe; and repeating steps c and d as many times as needed.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
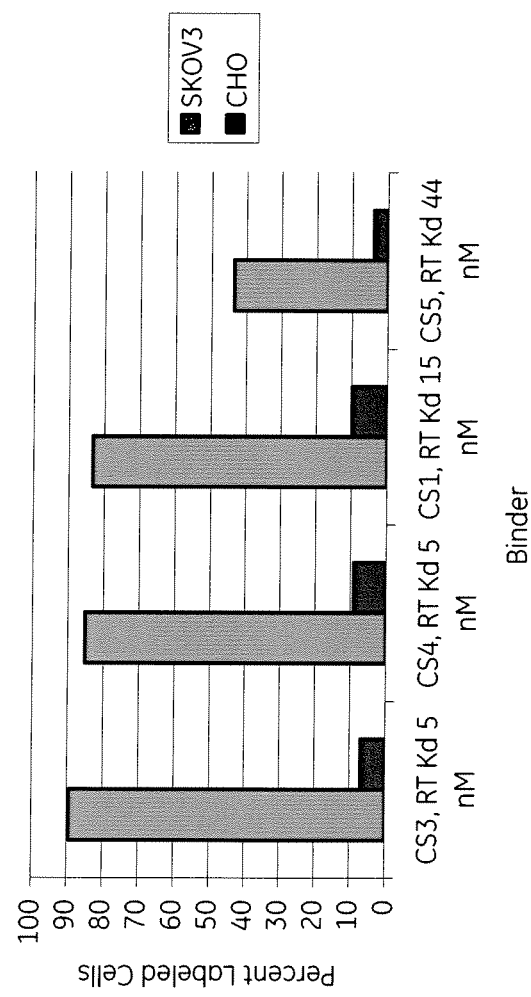
FIG. 1 is a graph showing an example of comparative binding of 2-helix binders to different types of cells.

To more clearly and concisely describe the subject matter of the claimed invention, the following definitions are provided for specific terms that are used in the following description and the claims appended hereto.

As used herein, the term "molecular switch" refers to a chemical moiety that can be switched between two or more states. Switch may be reversible or irreversible. This shift between states may be caused in response to one or more external stimuli including various environmental factors or ligands administered individually or in combination. Examples of molecular switches include but are not limited to pH switches, photochromic, chiroptical, host-guest switches, thermal switches, magnetic switches or electrical switches.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab')$_2$, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies), polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions and cells isolated from mammals including, humans. Biological samples also may include sections of the biological sample including tissues (e.g., sectional portions of an organ or tissue). Biological samples may also include extracts from a biological sample, for example, an antigen from a biological fluid (e.g., blood or urine).

A biological sample may be of prokaryotic origin or eukaryotic origin (e.g., insects, protozoa, birds, fish, reptiles). In some embodiments, the biological sample is mammalian (e.g., rat, mouse, cow, dog, donkey, guinea pig, or rabbit). In certain embodiments, the biological sample is of primate origin (e.g., example, chimpanzee or human).

As used herein, the term "probe" refers to an agent having a binder and a signal generator. In some embodiments, the binder and the signal generator of the probe are embodied in a single entity (e.g., a radioactive or fluorescent molecule capable of binding a target). In alternative embodiments, the binder and the signal generator are embodied in discrete entities (e.g., a primary antibody capable of binding target and labeled secondary antibody capable of binding the primary antibody). When the binder and signal generator are separate entities they may apply to a biological sample in a single step or multiple steps.

The binder and signal generator to the binder may be attached directly (e.g., via a radio-labeled atom incorporated into the binder or indirectly (e.g., through a linker, which may include a cleavage site) and applied to the biological sample in a single step. In some embodiments, the binder and the signal generator are separate entities that are pre-attached prior to application to the biological sample and applied to the biological sample in a single step. In other embodiments, the binder and the signal generator are separate entities that are applied to the biological sample independently and combine following application.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators include one or more of a chromophore, a fluorophore, a Raman-active tag, or a radioactive label. As stated above, with regard to the probe, the signal generator and the binder may be present in a single entity (e.g., a target binding protein with a fluorescent label or radiolabel) in some embodiments. And, in other embodiments the binder and the signal generator are discrete entities (e.g., a receptor protein and a labeled-antibody against that particular receptor protein) that associate with each other prior to or upon introduction to the sample.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example TEXAS RED (sulfonyl chloride derivative of sulforhodamine 101), Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2' disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl] naphthalimide-3,5disulfonate (Lucifer Yellow VS), N-(4-anilino-1-naphthyl)maleimide, anthranilamide, Brilliant Yellow, coumarin, coumarin derivatives, 7-amino-4-methyl-coumarin (AMC, Coumarin 120), 7-amino-trifluoromethyl-couluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosanilin; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (TEXAS RED); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, pyrelium dyes and squaraines.

As used herein, the term "solid support" refers to an article on which analytes or binders may be immobilized. Binders or analytes may be immobilized on the solid support by physical adsorption, by covalent bond formation, or by combinations thereof. A solid support may include a polymeric, a glass, or a metallic material. Examples of solid supports include a membrane, a microtiter plate, a bead, a microfluidic chip, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about $10^5$ $M^{-1}$ under ambient conditions (i.e., a pH of about 6 to about 8 and temperature ranging from about 0° C. to about 37° C.).

As used herein, the term "target or analyte," refers to the component of a biological sample or other sample of interest that may be detected or isolated when present in the sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), and lipids. The target may also include chemical or biological agents as well as whole cells.

As used herein, the term "peptide" refers to a sequence of amino acids connected to each other by peptide bonds between the alpha amino and carboxyl groups of adjacent amino acids. The amino acids may be the standard amino acids or some other non standard amino acids. Some of the standard nonpolar (hydrophobic) amino acids include alanine (Ala), leucine (Leu), isoleucine (Ile), valine (Val), proline (Pro), phenylalanine (Phe), tryptophan (Trp) and methionine (Met). The polar neutral amino acids include glycine (Gly), serine (Ser), threonine (Thr), cysteine (Cys), tyrosine (Tyr), asparagine (Asn) and glutamine (Gln). The positively charged (basic) amino acids include arginine (Arg), lysine (Lys) and histidine (His). The negatively charged (acidic) amino acids include aspartic acid (Asp) and glutamic acid (Glu). The non standard amino acids may be formed in body, for example by posttranslational modification, some examples of such amino acids being selenocysteine and pyrolysine. The peptides may be of a variety of lengths, either in their neutral (uncharged) form or in forms such as their salts. The peptides may be either free of modifications such as glycosylations, side chain oxidation or phosphorylation or comprising such modifications. Substitutes for an amino acid within the sequence may also be selected from other members of the class to which the amino acid belongs. A suitable peptide may also include peptides modified by additional substituents attached to the amino side chains, such as glycosyl units, lipids or inorganic ions such as phosphates as well as chemical modifications of the chains. Thus, the term "peptide" or its equivalent may be intended to include the appropriate amino acid sequence referenced, subject to the foregoing modifications, which do not destroy its functionality.

As used herein, the term "nucleotide" refers to both natural and modified nucleoside phosphates. The term "nucleoside" refers to a compound having a purine, deazapurine, pyrimidine or a modified base linked at the 1' position or at an equivalent position to a sugar or a sugar substitute (e.g., a carbocyclic or an acyclic moiety). The nucleoside may contain a 2'-deoxy, 2'-hydroxyl or 2',3'-dideoxy forms of sugar or sugar substitute as well as other substituted forms. The sugar moiety in the nucleoside phosphate may be a pentose sugar, such as ribose, and the phosphate esterification site may correspond to the hydroxyl group attached to the C-5 position of the pentose sugar of the nucleoside. A nucleotide may be, but is not limited to, a deoxyribonucleoside triphosphate (dNTP). Deoxyribonucleoside triphosphate may be, but is not limited to, a deoxyriboadenosine triphosphate (2'-deoxyadenosine 5'-triphosphate or dATP), a deoxyribocytosine triphosphate (2'-deoxycytidine 5'-triphosphate or dCTP), a deoxyriboguanosine triphosphate (2'-deoxyguanosine 5'-triphosphate or dGTP) or a deoxyribothymidine triphosphate (2'-deoxythymidine 5'-triphosphate or dTTP).

The term "oligonucleotide", as used herein, refers to oligomers of nucleotides or derivatives thereof. Throughout the specification, whenever an oligonucleotide is represented by a sequence of letters, the nucleotides are in 5'→3' order from left to right. In the letter sequence, letter A denotes adenosine, C denotes cytosine, G denotes guanosine, T denotes thymidine, W denotes A or T, and S denotes G or C. N represents a random nucleic acid base (e.g., N may be any of A, C, G, U, or T). A synthetic, locked, random nucleotide is represented by +N and a phosphorothioate modified random nucleotide is represented by *N.

"Nucleic acid," or "oligonucleotide", as used herein, may be a DNA, or an RNA, or its analogue (e.g., phosphorothioate analog). Nucleic acids or oligonucleotides may also include modified bases, backbones, and/or ends. Non-limiting examples of synthetic backbones include phosphorothioate, alkylphosphonate, boranophosphate, phosphoroamidate, peptide nucleic acid, morpholino, locked nucleic acid, xylose nucleic acid, or analogs thereof that confer stability and/or other advantages to the nucleic acids.

As used herein, the term cell refers to both eukaryotic and prokaryotic cells and includes cells derived from various tissues or organs, mature, immature, progenitor or stem cells. Term also includes cells manipulated in the laboratory to incorporate one or more desirable properties via, labeling, genetic engineering or any other means known in the art.

The term "stem cell" includes but is not limited to embryonic stem cells, adult stem cells, induced pluripotent stem cells, cancer stem cells, stem cells generated by somatic cell nuclear transfer. Stem cells may be isolated from blood, bone marrow, adipose or other tissues and organs.

The terms "molecule of interest" or "analyte" are used interchangeably. In some embodiments, the molecule of interest can be determined by the type and nature of analysis or separation required for the sample. In some embodiments, the analysis can provide information about the presence or absence of a molecule of interest in the sample. In another embodiment, an analysis can provide information on a state of a sample. For example, if the sample includes a drinking water sample, the analysis may provide information about the concentration of bacteria in the sample and thus the potability of the sample. Similarly, if the sample includes a tissue sample, the methods disclosed herein can be used to detect molecule(s) of interest that can help in comparing different types of cells or tissues, comparing different developmental stages, detecting the presence of a disease or abnormality, determining the type of disease abnormality or investigating the interactions between multiple molecules of interest.

In one embodiment, switchable affinity binders can be developed via molecular design and incorporation of environmentally sensitive elements directly into the molecular backbone of the binder. This enables a binder platform where specific elements that confer a consistent molecular change (steric rearrangement, electrical charge, etc) in response to a set environmental change are conserved, while other molecular elements that form a binding/target recognition pocket can be changed. In this way the switchable binder scaffold can be modified to recognize different targets while retaining sensitivity to a specific environmental change. This approach offers improved consistency of release mechanism and magnitude due to the conservation of the switchable backbone elements, but increases the difficulty of developing a high affinity binder against a desired target by limiting the number and location of affinity sequences that are allowed to change.

In another embodiment, switchable affinity binders can be prepared by selecting or designing non-switchable binders against specific targets of interest using any of the techniques commonly known to those skilled in the art and then chemically modifying the resulting binders via attachment of environmentally-sensitive moieties to create an environmentally-responsive switchable binder. This embodiment allows increased flexibility in the design and selection of the affinity binder as no portion of the scaffold must be conserved from one target to the next so long as sufficient chemical handles are present to allow subsequent modification. However, this same flexibility in scaffold backbone stipulates that binders against different targets (or even different binders against the same target) will offer different sensitivities to modification and hence, will often demonstrate differing levels of sensitivity to the desired environmental cue based on efficiency, location, etc of the molecular switch modifications.

Although the method of preparation may vary depending upon the binder scaffold and development methods utilized, the invention can be applied to numerous affinity binders by the selection of an appropriate environmental switch. A non-exhaustive list of potential affinity binders includes antibodies, antibody fragments, affibodies and peptide-based binders. Each of these affinity scaffolds offer distinct advantages and disadvantages that vary depending upon the intended application and have been reviewed at length in the literature. For the purpose of one or more of the embodiments, so long as the affinity binder selected is capable of direct or indirect addition of environmentally sensitive molecular switches the exact choice is left to the discretion of the user.

For the purposes of one or more of the embodiments, a molecular or environmental switch is defined as a chemical moiety integrated or appended to the binder that undergoes a distinct physical change (e.g. conformational shift, electrical change, change in pI, etc) in response to an external stimulus. By modifying the choice of molecular switch it is possible to develop switchable binders that are sensitive to a wide variety of environmental cues and a wide variety of stimuli intensity. These environmental stimuli may include, but are not limited to temperature, pH, salt/ion concentration, exposure to light of specific wavelengths, introduction of chemical compounds, etc. In addition to incorporating a single type of switch and using a single stimulus, it is feasible to use multiple types of switches on the same binder and/or apply multiple stimuli.

By careful selection, it is further possible to identify subclasses of these switches that respond to moderate stimuli changes and intensity such that both the pre- and post-switch environmental conditions are amenable to biological samples such as nucleic acids, proteins, cells, tissues, and animals. This enables their use in in situ, in silico, in vitro, and in vivo applications without risk of damaging or modifying the target and allows them to be utilized for such tasks as biological separations, target labeling and visualization, multiplexing analysis, and sensors. Potential molecular switches and their associated advantages and disadvantages have been extensively discussed in the literature. For the purpose of one or more of the embodiments, any of these may be utilized so long as a means of integrating them directly into the backbone of the selected affinity binder, or of indirectly appending them to the binder, can be devised without significantly disrupting the ability of the affinity binder to recognize the desired target.

When constructed, regardless of the preparation method utilized, the resulting switchable affinity binders offer an initial affinity toward their target capable of high selectivity, high specificity binding under one environmental condition, but demonstrate a drastic decrease in binding affinity under a second environmental condition. This decrease in binding affinity is sufficient enough that the binders can be removed from their target through a gentle wash step, leaving the sample in an unmodified, pre-analysis state.

Such switchable affinity binders can be used in any format that does not inhibit the initial target binding, or subsequent target release, of the modified affinity binder. For example, solution based or solid-immobilized states. This includes, but is not limited to, directly conjugated dye-affinity binder ligands utilized in solution, such as for fluorescent activated cell sorting, live or fixed cell staining, and tissue sample staining, as well as immobilization on a solid surface, such as microscope slides, magnetic or chromatographic beads, flow chamber surfaces, sensor arrays, etc. This flexibility allows switchable affinity binders to be utilized in various applications, including but not limited to cell and tissue analysis, cell and protein separations, renewable sensors, etc.

In some embodiments, the target comprises, but is not limited to, one or more biological cells. For example, cells may include prokaryotic and eukaryotic origin. Eukaryotic cells may be of any classification, including but not limited to insect, amphibian, avian, mammalian, and human. Suitable human cells include clinically relevant cells such from the endoderm, ectoderm, and mesoderm, such as stem cells, cancer cells, and blood cells.

In some embodiments, the target comprises, but is not limited to, one or more biological agents. For example, biological agents may comprise pathogens, toxins, or combinations thereof. Biological agents can include prions, microorganisms (viruses, bacteria and fungi) and some unicellular and multicellular eukaryotes (for example parasites) and their associated toxins. Pathogens are infectious agents that can cause disease or illness to their host (animal or plant). Pathogens can include one or more of bacteria, viruses, protozoa, fungi, parasites, or prions.

In some embodiments, separation comprises, but is not limited to, isolation of a protein, antibody or other biological agent form a biological sample from a natural source or produced in a laboratory. Examples include, but are not limited to, therapeutic proteins, such as insulin, therapeutic or diagnostic antibodies, vaccines, enzymes or hormones.

EXAMPLES

The abbreviations used in the Examples section are expanded as follows: "min": minutes; "h": hour(s); "s": seconds; "rt": room temperature; "mg": milligrams; "mL": milliliters; "mg/mL": milligrams per milliliter; "mmol": millimoles; "µL ": microliter; "KDa": kilodaltons; "MALDI-TOF-MS": Matrix Assisted Laser Desorption Ionization Time-of-Flight Mass Spectrometry; "HPLC": High Pressure Liquid Chromatography; "(LC-MS)" Liquid Chromatography Mass Spectrometry, "ESI-MS": Electrospray Ionization Mass Spectrometry, "TFA": Trifluoroacetic acid; "HOAc": acetic acid; "DMSO": Dimethylsulfoxide; "DMF": Dimethylformamide; "DVB": divinylbenzene; "DTT": dithiothreitol; "NMM": N-methylmorpholine; "HCl": hydrochloric acid; "MeCN": acetonitrile; "NHS": N-hydroxy succinimidyl; "PBS": phosphate buffered saline; "SP": 1-(β-carboxyethyl) -3,3-dimethyl-6'-nitrospiro(indoline-2,2'-2H-benzopyran; "MWCO": Molecular Weight Cut Off; "Fmoc": 9-fluorenylmethyl carbamate; "HBTU": ortho-benzotriazole-N,N,N'N'-tetramethyluronium hexafluorophosphate; "TIPS": triisopropylsilane; "EDT": ethanedithiol; "Rink amide resin LS": 4-(2',4'-dimethoxyphenyl-Fmoc-aminomethyl)-phenoxy resin, 100-200 mesh. Unless otherwise noted, all reagent-grade chemicals were used as received, and Millipore water was used in the preparation of all aqueous solutions.

Example 1

Preparation of Biotin-GSGS-CS1 (SEQ ID NO: 1)

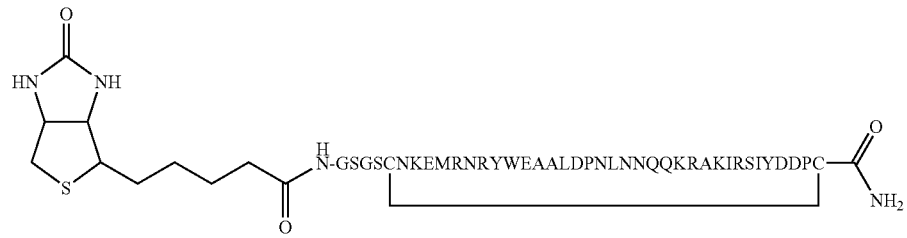

Linear peptide (Biotin-GSGSCNKEMRNRYWEAALD-PNLNNQQKRAKIRSIYDDPC (SEQ ID NO: 2)) was synthesized using standard solid phase techniques with N-α-Fmoc-protected amino acids using 0.2 mmol/g substitution Rink Amide Resin LS on a 40-100 µmol scale. The peptide was synthesized using a Symphony peptide synthesizer (Protein Technologies Inc.). The resin was swelled for one hour in methylene chloride, and was subsequently washed with DMF for 30 min when the methylene chloride was exchanged. Each coupling reaction was carried out at room temperature with HBTU as coupling reagent and NMM as the base. For each step, the coupling agent and the amino acid were each delivered at a scale of five equivalents relative to the estimated resin capacity. Double couplings were carried out for most residues except for the residues 2-5. The coupling time was 30 min (40 min for first coupling) for a single coupling and 2×20 min for a double coupling. The reactions did not perturb the side-chains of the amino acids, which were protected with an acid labile group or, in the case of cysteines, an acid and base stable acetamidomethyl (Acm) group was used. Following each coupling reaction, the N-terminal Fmoc-protected amine was deprotected by applying 20% piperidine in DMF at room temperature for 15 min. After final amino acid coupling and deprotection of the N-terminal Fmoc protecting group, biotin was conjugated using the same procedure as used for other amino acid residues. Solid support was then washed with DMF six times and DCM six times, and dried for 50 min by passing nitrogen through the reaction vessel.

Cleavage and deprotection: The peptide was cleaved from the support and the side chains were deprotected (except Cysteine) by agitating the support with 1.2 mL of a mixture of TFA:EDT:Water:TIPS in a ratio of 94:2.5:2.5:1 per 100 mg of starting resin (at the beginning of peptide synthesis), for about 2-2.5 h. The mixture was filtered through glass wool and the resin was washed with 2×0.5 mL TFA. Filtrate and washings were cooled in solid dry ice and diluted with cold ether (~10-15 land filtrate). The suspension was centrifuged at 3000 rcf at 4° C. for 10 min Supernatant was decanted and residue was resuspended in cold ether (~20 ml) and the process of centrifugation and decantation was repeated 3 times. Final residue was dissolved in water and lyophilized Deviations from above process, and further details, for each peptide, are described below.

Oxidation (cyclization: Crude linear peptide (6 mg) was dissolved in 2 mL of 50% HOAc. The solution was diluted with 18 mL of 1N HCl. To this solution, 244.4 µL of iodine solution (0.1 M, prepared by mixing 1 volume of 1N (0.5M) $I_2$ solution with 4 volumes of 50% HOAc) was added and the mixture was stirred for 90 minutes. The reaction was quenched by dropwise addition of 1M sodium thiosulfate until no color remained. The resulting mixture was purified by reverse phase HPLC on an AKTA purifier using the following method: 0-25% B 6.875 CV (column volumes), 25-35% B 41.25 CV and 35-100% B 1.875 CV, Column: Xterra MS C18 19×100 mm, 5 µm particle size, Flow rate: 10 ml/min, Buffers: A, 0.1% TFA in water, B, 0.1% TFA in acetonitrile (ACN). When the main peak started eluting, fractions were manually collected. A single fraction was found to be pure by analytical HPLC and was lyophilized. MS (monoisotopic mass): Calc: 4763.2, Found: 4763.8.

Example 2

Preparation of Biotin-VENK-CS2 (SEQ ID NO: 3)

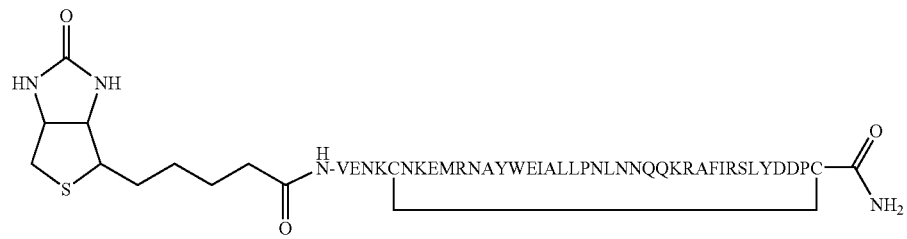

Linear peptide (Biotin-VENKCNKEMRNAYWEIALLP-NLNNQQKRAFIRSLYDDPC (SEQ ID NO: 4)) was prepared in a manner identical to that described for Biotin-GSGS-CS1(SEQ ID NO: 1).

Oxidation (cyclization) of Biotin-VENK-CS2 (SEQ ID NO: 3): The oxidation (cyclization) of Biotin-VENK-CS2 (SEQ ID NO: 3) was conducted in a manner identical to that described for Biotin-GSGS-CS1 (SEQ ID NO: 1). The crude mixture was initially purified on a SepPak C18 plus column using a step wise gradient starting with 100% of 0.1% TFA in water and ending with 100% of 0.1% TFA in acetonitrile with steps of 10% change up to 50% and then jump to 100%. Most of the product eluted with 40% B. After lyophilization, residue was dissolved in 300 uL water and was further purified on analytical HPLC (column: Xterra C18 4.6×50 mm, 5 um particle size, flow rate 1 ml/min, gradient method same as listed above for purification of Biotin CS1 in three runs. Major peak was collected, combined and lyophilized. After lyophilization, analytical HPLC showed a single peak shifted back to 20.8 min. Mass (monoisotopic): Calc: 4919.3, Found: 4920.3.

Example 3

Preparation of Cy5-VENK-CS3 (SEQ ID NO: 5)

Linear peptide (Cy5-VENK$^h$CNKEMRNRYWEAALDP-NLNNQQKRAKIRSIYDDP$^h$C (where $^h$C stands for homocysteine) (SEQ ID NO: 6)) dye-labeled linear peptide was prepared and purified as described above for Biotin-GSGS-CS1 (SEQ ID NO: 1) with some modification for dye attachment. In addition an acid-labile group (trityl group was used for Cysteine side chain protection Dye attachment: After final amino acid addition and N-terminal amino group deprotection, resin was washed and dried as described above for Biotin-GSGS-CS1 (SEQ ID NO: 1). A portion of the solid support (10 µmol scale) was placed back on the peptide synthesizer, swollen in dichloromethane (DCM) for 30 minutes and washed three times each with DCM and DMF followed by suspending the treated solid support in 2 mL of anhydrous DMF. To the suspension about 10 μL of NMM was added followed by the addition of a solution of Cy5-NHS ester in 0.5 ml of anhydrous DMF. The dye container was rinsed with 0.5 ml of DMF and this solution was also added to the reaction mixture. The reaction mixture was allowed to stand overnight with agitation about every 30 s by bubbling nitrogen through the suspension. The dye solution was then allowed to drain and the support was repeatedly washed with DMF (9 times) and then DCM (6 times) before drying. The support was then dried by passage of nitrogen for 30 min. Cleavage and deprotection was performed as described above for linear Biotin-GSGS-CS1 (SEQ ID NO: 1). Crude material was purified by the method used for cyclized Biotin-GSGS-CS1 (SEQ ID NO: 1).

Oxidation (cyclization): Two methods were tried for oxidation. In the first, a portion of the material from the linear peptide purification was dissolved in 4 mL of 0.01M sodium phosphate (pH 7.8). After bubbling air through the solution for two minutes, the container was wrapped with aluminum foil and covered with a Chemwipe on top (to allow for air circulation). The mixture was stirred at room temperature and the reaction was followed by HPLC. After 1 day, two overlapping peaks were observed in about equal proportions. After 4 days, the reaction was complete. A sample was submitted for LCMS and showed formation of oxidized product (Observed mass 5386.1 vs 5388.7 for the linear peptide).

In the second method, remaining material from the linear peptide purification was taken in 9 mL of 0.01 M sodium phosphate (pH 7.8). To this, 1 mL DMSO was added and the mixture was stirred at room temperature in the dark. After overnight stirring, only a single peak was observed in the region of starting material and product. Reaction mixtures from two batches were combined and purified on an AKTA purifier using the same method as described above. Product eluted in fractions 14 & 15, which were combined and lyophilized to give a blue solid. HPLC showed a single peak. Mass (monoisotopic): Calc: 5386.5, Found: 5386.1

Example 4

Preparation of Cy5-VENK-CS4 (SEQ ID NOS 7-9, respectively, in order of appearance)

Cy5-VENK-CS4 (SEQ ID NOS 7-9) where $^hC$ stands for homocysteine and $^iBu$ stands for isobutyric acid) was prepared and purified as described above for Cy5-VENK-CS3 (SEQ ID NO: 5). Oxidation method used was DMSO facilitated oxidation. Analytical HPLC showed 97% purity. Mass (monoisotopic): Calc: 5414.3, Found: 5414.5.

Example 5

Preparation of Cy5-VENK-CS1 (SEQ ID NO: 14)

Cy5-VENK-CS1 (SEQ ID NO: 14) was synthesized and purified as described above for Cy5-VENK-CS4 (SEQ ID NOS 7-9). Analytical HPLC showed a single species with a retention time of 8.3 min. Mass (monoisotopic) Calc: 5358.3, Found 5358.6.

Example 6

Preparation of Cy5-VENK-CS5 (SEQ ID NO: 13)

Cy5-VENK-CS5 (SEQ ID NO: 13) (Cy5-VENK-FNKEMRNRYWEAALDPNLNNQQKRAKIRSIYDDPS (SEQ ID NO: 13)): linear peptide was synthesized and purified as described above for linear peptide intermediate for Cy5-VENK-CS3 (SEQ ID NO: 5). Three sets of fractions were collected and lyophilized: fractions 14-15 (purity 96.5%, slightly broad peak with retention time 8.9 min), fractions 16-19 (purity 97.5%, sharp peak, retention time 9.4 min) and fractions 20-22 (purity 98%, sharp peak retention time 9.4 min). Mass (monoisotopic): Calc: 5388.4, Found: 5389.4. This peptide has no cysteines and its synthesis involves no cyclization step.

Example 7

Preparation of Biotin-LC-LC-VENK-CS4 (SEQ ID NO: 14)

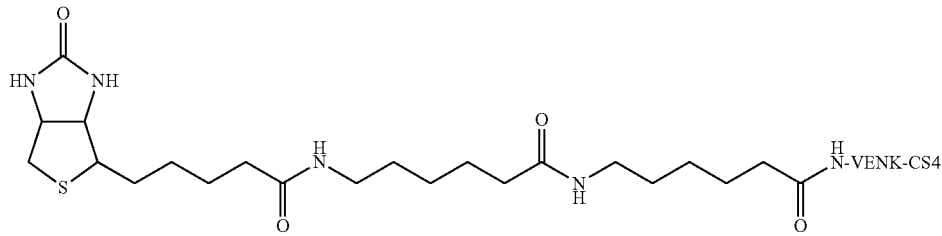

Biotin-LC-LC-VENK-CS4 linear peptide (SEQ ID NO: 14) was synthesized as described above for Cy5 labeled peptides. Commercially available Biotin-LC-LC-NHS ester (14mg) and twice the amount of resin (20 µmol equivalent) were used. Purification was performed via reverse phase HPLC on the AKTA purifier under the following conditions: 20% B for 6.25 CV, 20-30% B in 35.5 CV and 30-100% B in 2.5 CV. Mass (monoisotopic): Calc: 5229.3, Found: 5230.6.

Oxidation of Biotin-LC-LC-VENK-CS4 (SEQ ID NO: 14): Combined material from both column purifications was taken in 4.5 mL 0.01 M sodium phosphate (pH 7.8). To this 450 µL DMSO was added and the mixture was stirred at room temperature overnight. Reaction mixture was filtered to remove insoluble material and purified on an AKTA purifier using a gradient method (20% B for 25 CV, 20-30% B in 37.5 CV and 30-100% B in 2.5 CV, Column: Xterra MS C18 19×100 mm, flow rate 10 ml/min, Solvent A: 0.1% TFA/water and Solvent B: 0.1% TFA/ACN). Main fraction was analyzed by MALDI and was found to be the desired product. Mass (monoisotopic): Calc: 5229.3, Found 5227.0

Example 8

Preparation of Biotin-PEG12-VENK-CS3 (SEQ ID NO: 13)

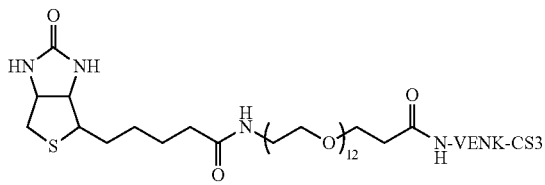

Biotin-PEG12-VENK-CS3 linear peptide (SEQ ID NO: 13) was synthesized as described above for Cy5-labeled peptides. 26 µmol of resin-supported CS3 was swelled as above and then suspended in ~3 mL DMF containing 15 µL of NMM. Commercial Biotin-PEG12-NHS from Quanta Biodesign (80 mg) was dissolved in 1 mL anhydrous DMF. A portion of this (0.6 mL) was added to CS3 resin. Mixing and washings were performed as described for dye labeled peptides. Cleavage and further work up was also performed as described above.

Oxidation of Biotin-PEG12-VENK-CS3 (SEQ ID NO: 13): A portion of crude Biotin-PEG12-VENK-CS3 (SEQ ID NO: 13) (10 mg) was dissolved in 10 mL of 0.01M sodium phosphate (pH 7.8) buffer. To this 1 mL of DMSO was added and the mixture was stirred at room temperature overnight. Reaction was followed by analytical HPLC. LC method: Column used, Xterra RP 4.6×50 mm, solvent A 0.1% TFA/water, solvent B 0.1% TFA/ACN, flow rate: 1 mL/min, gradient: 0-25% B in 30 min (37.5 CV), 25-35% B in 30 min (37.5 CV). Crude mixture was purified on an AKTA purifier using Xterra MS C18 19×100 mm column using the same buffers and gradient method after conversion to column volumes. Flow rate was 10 ml/min. Eluted product was lyophilized. HPLC showed a single peak. Mass: Calc: 5572.3, Found: 5573.2.

Example 9

Preparation of Biotin-PEG12-VENK-CS4 (SEQ ID NO: 14)

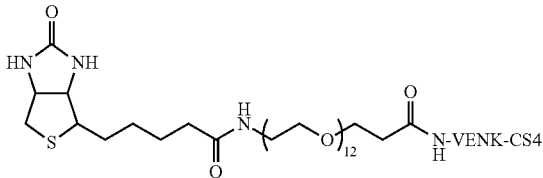

Biotin-PEG12-VENK-CS4 linear peptide (SEQ ID NO: 14) was prepared in a manner identical to that described for Biotin-PEG12-VENK-CS3 (SEQ ID NO: 13).

Oxidation of Biotin-PEG12-VENK-CS4 (SEQ ID NO: 14): Oxidation was performed at 2× higher dilution than most of the prior oxidation reactions to decrease insoluble product formation (possibly due to oligomerization). Crude Biotin-PEG12-CS4 (10 mg) was dissolved in 20 mL 0.01M sodium phosphate (pH 7.8). To this 2 mL DMSO was added and mixture was stirred at room temperature. After 2 days, the crude product was filtered and purified on AKTA using the following method: 0-25% B in 37.5 CV, 25-35% B in 37.5 CV and 35-100% B in 1.875 CV, Column Xterra MS C18 19×100 mm, flow rate 10ml/min, Solvent A: 0.1% TFA/water and Solvent B: 0.1% TFA/ACN. Majority of the main peak eluted in a single fraction which was lyophilized and analyzed by HPLC and MALDI-TOF-MS. HPLC showed a purity of only 85%. Further purification was performed by using analytical HPLC. Mass: Calc: 5600.3, Found 5600.5.

Example 10

Demonstration of Cell Binding and Release of 2-Helix Peptide Binders in Solution SKOV-3 human ovarian cells (ATCC) were used as a positive control for Her-2 expression. SKOV-3 cells were cultured according to the ATCC protocol in McCoy5a media with 10% FBS and 1% Penicillin-Streptomycin.

Chinese Hamster Ovary cells (CHO, ATCC) were cultured in F-12K media supplemented with 10% FBS and 1% Penicillin-Streptomycin according to the ATCC recommendations and were used as negative control.

For visualization, cells were labeled with Cell Tracker Green (Invitrogen) at 1 μM final concentration in PBS. Cells with dye were incubated for 30 min at 37° C. on a rocker, centrifuged at 1000 rpm, washed with PBS one time, and resuspended in PBS at the desired concentration.

Cell Binding in Solution: SKOV-3 and CHO cells were blocked with 1% BSA for 15 min at 4° C. with rocking (200 μL total volume/sample). Labeled Binder or control labeled anti-Her2 Ab was added to the cells ($10^6$ cells/sample) at a final concentration of 5 μg/mL for 30 min at 4° C. on a rocker. The unbound and non-specific binding fractions were washed away in PBS by spinning the cells at 1000 rpm for 5 min Samples were then kept in 1% Paraformaldehyde (PFA) at 4° C. in a total volume of 200 μL. Cells were analyzed on a Beckman Coulter FC500 flow cytometer.

Cell Release in Solution: After binding as described above but prior to storage in paraformaldehyde, samples used for estimating the release fraction were incubated at 37° C. for 30 min on a rocker. After a 15 min incubation at 37° C., cells were spun down and the supernatant was removed. The cell pellet was then resuspended at 37° C. in PBS and was further incubated at 37° C. for another 15 min. At the end, the cells were spun down and resuspended in 200 μL 1% PFA and kept at 4° C. Cells were analyzed on a Beckman Coulter FC500 flow cytometer.

As shown in FIG. 1, Significant and selective binding of Her2-expressing SKOV-3 cells occurs with the Cy5 variants of the 2-helix binders CS1, 3-5, with minimal binding of these peptides to the negative control CHO cell line.

Figure 2:
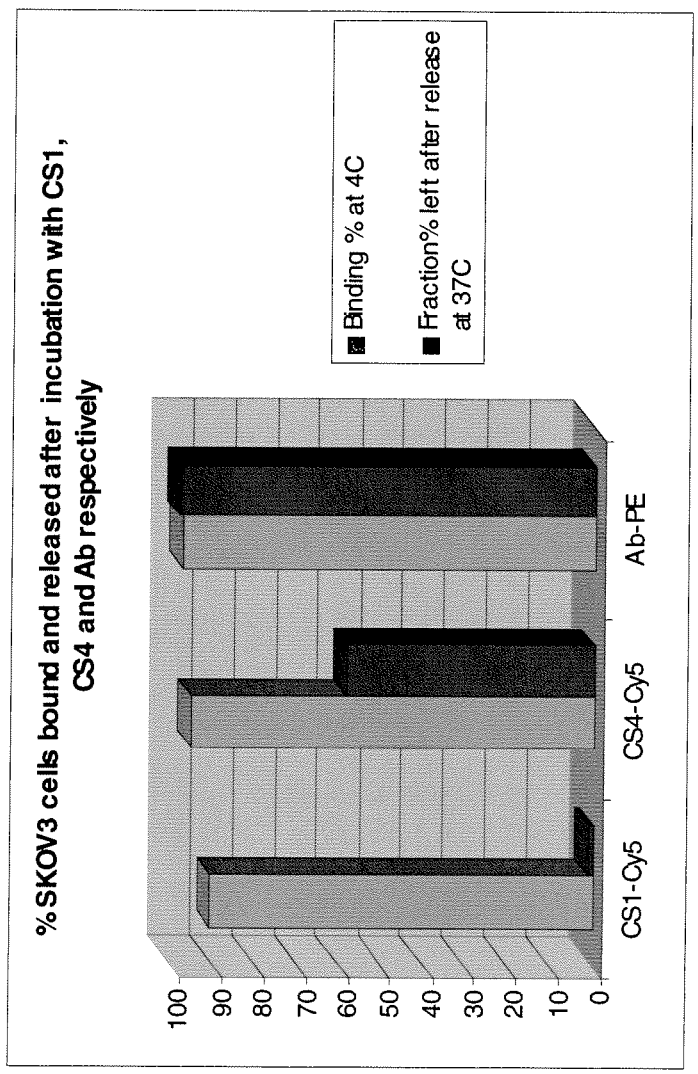
FIG. 2 is a graph showing an example of the percentage of SKOV3 cells bound and released after incubation with CS1, CS4 and a non-switchable Ab control.

FIG. 2 compares Cy5-VENK-CS1 (SEQ ID NO: 14) and Cy5-VENK-CS4 (SEQ ID NOS 7-9) binding and release to SKOV-3 cells with control anti-Her2 Ab. The control Ab remains completely bound to cells while the peptide binders exhibit significant levels of release following the temperature elevation.

Example 11

The Binding and Release of Cy5-VENK-CS4 (SEQ ID NOS 7-9) 2-helix peptide Binder to SKOV-3 Cells in a Mixed Cell Population in Solution SKOV-3 were prepared and labeled as described above in Example 10 and then mixed with unlabeled CHO cells to give 10% SKOV-3 cells and 90% CHO cells. Subsequent binding and release studies were carried out with Cy5-VENK-CS4 binder (SEQ ID NOS 7-9) as described above in Example 10.

Figure 3:
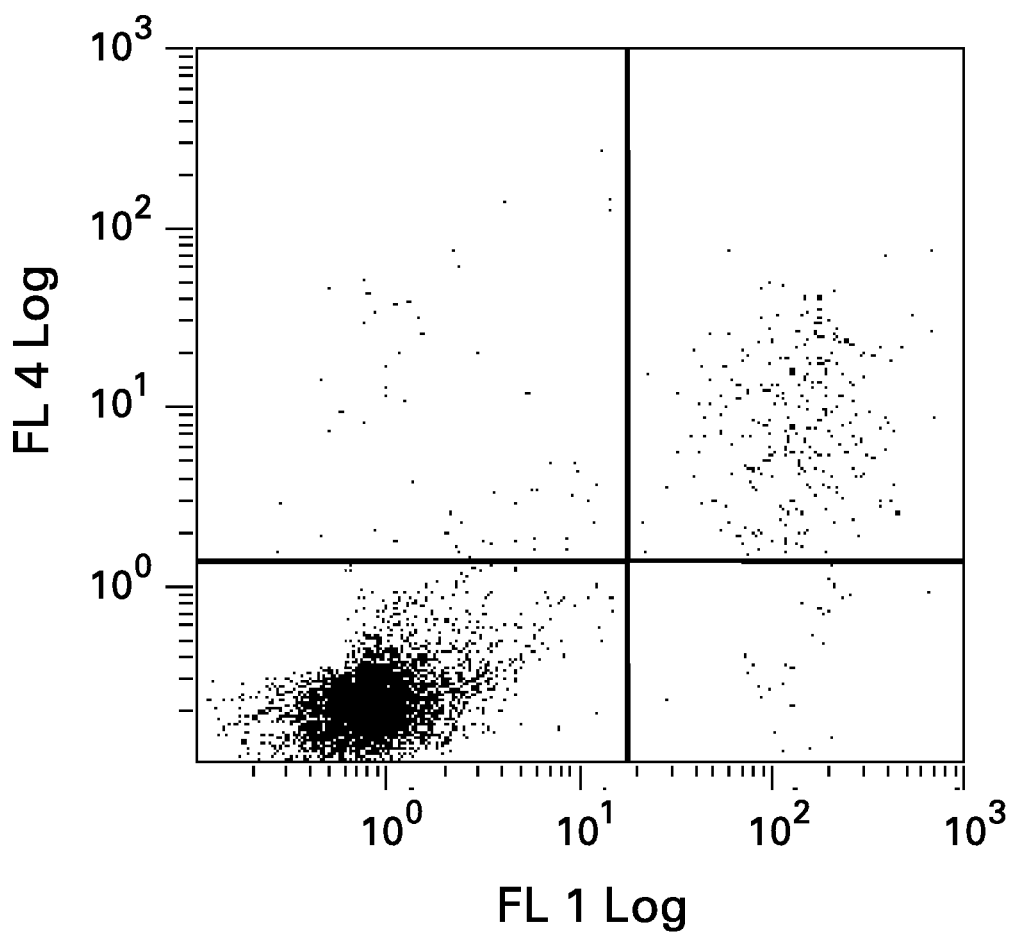
FIG. 3 is a graph showing an example of the selective capture and release of SKOV-3 cells from a mixed cell population comprised of CHO and SKOV-3 cell in 9:1 ratio.

FIG. 3 demonstrates selective capture of SKOV-3 cells in the presence of non-targeted CHO cells (SKOV-3 cells are captured at high efficiency while CHO cells remain unbound.

Example 12

The Cell Binding and Release of Biotin-PEG12-VENK-CS3 (SEQ ID NO: 13) 2-Helix Peptide Binder on a Solid Support Cell binding and bead capture: SKOV-3 and CHO cells ($10^6$ cells per sample) were blocked with 1% BSA in PBS for 15 min at 4° C. before the addition of 200 μL of 5 μg/mL biotin-PEG12-VENK-CS3 binder (SEQ ID NO: 13). This mixture was then incubated at 4° C. for 30 min with gentle shaking. Samples were then centrifuged and washed twice in PBS to remove the excess, unbound biotin-PEG12-VENK-CS3 (SEQ ID NO: 13). Dynal Streptavidin magnetic beads (Invitrogen) were washed three times with PBS at rt before the addition of 150 μL of this bead slurry to each of the cell-binder mixtures for 30-60 min. After incubation, beads were captured with a magnet and unbound cells were washed off at 4° C. prior to imaging to quantify bound cells.

Cell release from beads: The above cell-binder-bead mixtures were removed from 4° C. conditions to 37° C. incubation. After 15 min incubation at 37° C., beads were pulled down with a magnet and released cells were washed off. Incubation and washing was repeated one more time before imaging to quantify any unreleased cells. Visualization was achieved with a Typhoon 9410 fluorescent imaging system (GE Healthcare). Quantification of fluorescence was achieved using ImageQuant software (version 5.2, GE Healthcare).

Figure 4:
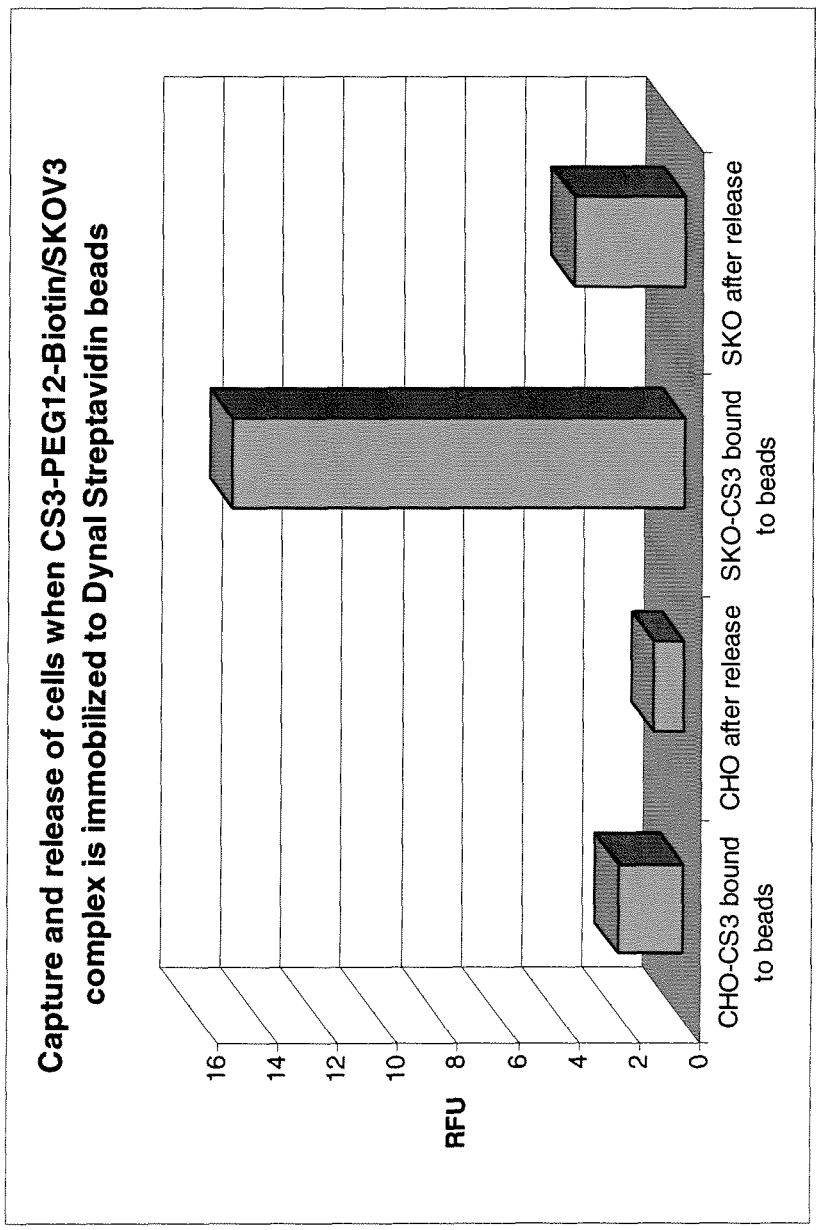
FIG. 4 is a graph showing an example of the capture and release of cells when CS3-PEG12-Biotin/SKOV3 complex is immobilized to Dynal Streptavidin beads.

FIG. 4 details the biotin-PEG12-CS3 bead-immobilized capture and release of cells. Following the trend of solution binding and release data, selective capture of the SKOV-3 cells is observed with this binder and a significant proportion of the bound SKOV-3 cells are released from the beads following incubation at 37° C.

Example 13

Preparation of αCD34-SP Antibody Conjugates for Cell Binding and Release

SP-NHS Synthesis: A modified version of the protocol originally published by Aizawa, et al. was used to synthesize the spiropyran precursor molecule SP. To a flask equipped with a magnetic stir bar were added 2,3,3-trimethylindolenine (3.2 mL, 20 mmol) and β-iodopropionic acid (4.0 g, 20 mmol). The resulting mixture was heated at 80° C. for 3 h before being cooled to room temperature (rt) and diluted with methanol (30-50 mL). Addition of ethyl acetate (150 mL) induced precipitation of the desired 1-carboxyethyl-2,3,3-trimethylindolenium iodide product (TMII). This pink solid was further washed several times with excess ethyl acetate, dried under reduced pressure, and used without further purification. Product identity and the relative purity were confirmed using TLC (5% MeOH/95% $CH_2Cl_2$).

To a clean reaction tube, were next added, TMII (0.5 mg, 1.39 mmol) suspended in 1.25 mL of methyl ethyl ketone (MEK) followed by addition of piperidine (125 μL, 1.27 mmol). This mixture was heated at 110° C. until complete dissolution of TMII was achieved. 5-nitrosalicyl aldehyde (250 mg, 1.91 mmol) dissolved in 500 μL MEK was added next and the resulting reaction solution was heated at 110° C. for 5 min. The crude product mixture was left overnight at rt before being diluted in methanol (10 mL). Addition of excess ethyl acetate (60 mL) induced SP product precipitation. This tan solid was then filtered, washed three times, dried for several hours under reduced pressure, and subsequently used without further purification.

A DMF solution of SP (10 mg, 26.3 mmol in 263 μL) was added to a dry reaction vial followed by addition of dicyclohexylcarbodiimide (DCC) (16 mg, 79 mmol) and N-hydroxysuccinimide (NHS) (9 mg, 79 mmol). The reaction mixture was sealed with parafilm, protected from light, and stirred for 4 h at rt. The resulting amber solution was filtered to remove the white solid urea precipitate before final concentration of the filtrate under vacuum to afford SP-NHS as an oily residue.

Following HPLC and ESI-MS confirmation of product identity and purity, SP-NHS was diluted to 67 μM in anhydrous DMF, sealed from moisture, and stored at −20° C. Analytical HPLC conditions: $H_2O$/0.1% TFA to MeCN/0.1% TFA linear gradient over 10 min on Xbridge C18 column, 2.5 μm, 1.0×50 mm (Waters) with UV monitoring at 254 and 345 nm. SP elution at 8.0 min, SP-NHS elution at 8.4 min ESI-MS for $C_{25}H_{23}N_3O_7$ (Calculated m/z=477.15, Found m/z=477.15).

Modification of αCD34 with SP: Anti-CD34 anti-human mouse monoclonal antibody of the IgG3,k isotype purchased from Lifespan (aCD34, 100 μg) was dialyzed overnight at 4° C. against 3.5 L of PBS buffer and then 3.5 L of 0.1 M $NaHCO_3$, pH 8.3 for 2 h at rt. The resulting sample was concentrated to 1-3 mg/mL (5-17 nmol) via centrifugal ultrafiltration. Protein concentration was determined by UV-Vis spectrophotometry and LDS-PAGE protein gel electrophoresis against known quantities of antibody. To 20 μL of this solution was added a 1 μL aliquot of SP-NHS diluted in anhydrous DMF to give a concentration of 5-5000 nM (1-1000 molar equivalents of SP-NHS relative to 1 equivalent of whole antibody). Reaction mixtures were incubated for 2 h. at rt or 15 h at 4° C. After this time, samples were subjected to Zeba desalting spin columns (Thermo Scientific) equilibrated with PBS/0.05% Tween-20 (PBST) and quantified for protein recovery and extent of modification via UV-Vis measurements and protein gel electrophoresis as before. Samples were stored at 4° C. for several weeks and used for subsequent cell binding and release assays as necessary.

Figure 5:
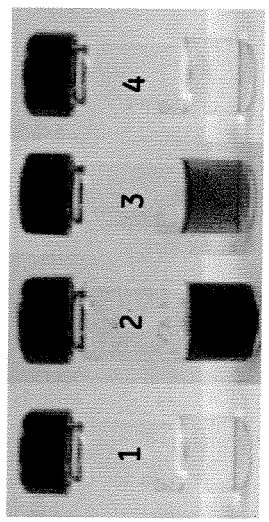
FIG. 5 shows examples of photoswitchable isomerization of SP when exposed to varying wavelengths of light and allowed to relax for varying periods of times.
Figure 6:
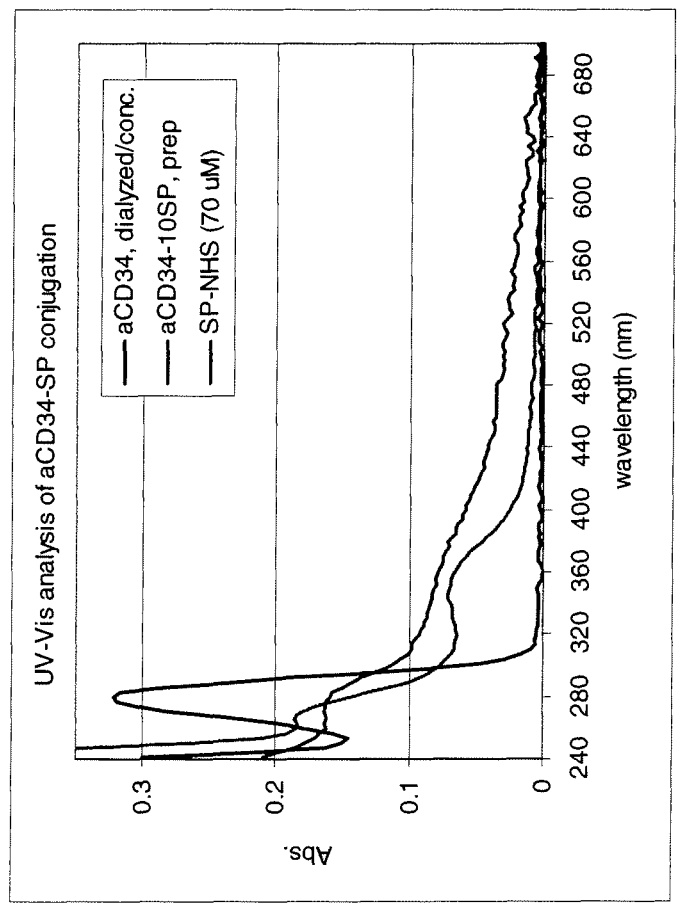
FIG. 6 is a graph of an example of a UV-Vis analysis of aCD34-SP conjugation.

FIG. 5 depicts the photoswitchable behaviour of SP in acetone as indicated by absorbance changes. FIG. 6 shows a UV-Vis spectral comparison of aCD34, SP-NHS, and αCD34-SP.

Example 14

Immobilized αCD34 Capture of CD34+ KG1a Cells

Cell lines and culturing conditions: The variant subline KG-1a (ATCC) of the human acute myelogenous leukemia cell line KG-1 as well as the promyelocytic cell line HL-60 (ATCC, catalog no. CCL-240) were each cultured and maintained at a concentration between $2\times10^5$ and $1\times10^6$ cells/mL according to the manufacturer's protocol. Briefly, cells were maintained in Iscove's Modified Dulbecco's Medium (IMDM) (ATCC) with 20% fetal bovine serum at 37° C. in an atmosphere of 5% $CO_2$. Subculturing was performed twice a week or as necessary.

Microplate cell binding assay: Native, modified, or control Abs were diluted to ~1 μg/mL in PBS/0.05% Tween-20/0.2% BSA (PBSTB) and added (100 μL/well) to Reacti-Bind Protein G Coated 96-Well Plates (Thermo Scientific) that had been washed three times with PBST just prior to Ab addition. Following 1 h incubation at 37° C., the Ab solution was removed and the plates were washed three times with PBS/0.1% BSA/2 mM EDTA (PBSBE).

KG1a or HL-60 cells of known concentration were removed from culture, centrifuged (1000 RPM, 5 min), washed once with Dulbecco's PBS (DABS), and centrifuged a second time. After removal of wash buffer, cells were resuspended in 10 mL of DABS, before addition of 1 μL of a 10 mM DMSO solution of CellTrackerGreen CFMDA, CellTracker Red CMTPX, or CellTrace Far Red DDAO-SE (Invitrogen). Labeling reactions were incubated for 30 min at 37° C. with gentle agitation on a culture tube rotisserie. Following centrifugation, the resulting labeled cells were washed once with PBSBE, centrifuged again, and resuspended in PBSBE to give a final concentration of 500 cells/ μL. Labeled cells were used immediately in microplate binding assays or were protected from light and placed on ice for use within a few hours.

To Ab-coated or control microplate wells were added 100 μL aliquots of labeled cell suspension mix. Following incubation, wells were washed three times via gentle pipette aspiration with 200 μL PBSBE. A final 100 μL portion of PBSBE was added to each well for fluorescent plate readings conducted on a Typhoon 9410 fluorescent imaging system (GE Healthcare). Quantification of fluorescence was achieved using ImageQuant software (version 5.2, GE Healthcare).

Example 15

Immobilized αCD34-SP Capture and UVA-Induced Release of CD34+ KG1a Cells Labeled with CellTracker Green CellTracker Green (CTG) cell labeling and antibody immobilization of 2 separate microplates were performed in a manner identical to Example 14. After cell addition, one plate was exposed to brightfield illumination for 30 min at rt while a second plate was exposed to 10 min of UVA radiation (365 nm using a benchtop transilluminator) along with 20 min dark incubation at rt (that is, 2×5 min UVA exposure separated by 20 minutes of dark incubation). Three PBSBE washes were then performed and the resulting cell retention was visualized and quantified as above.

Figure 7:
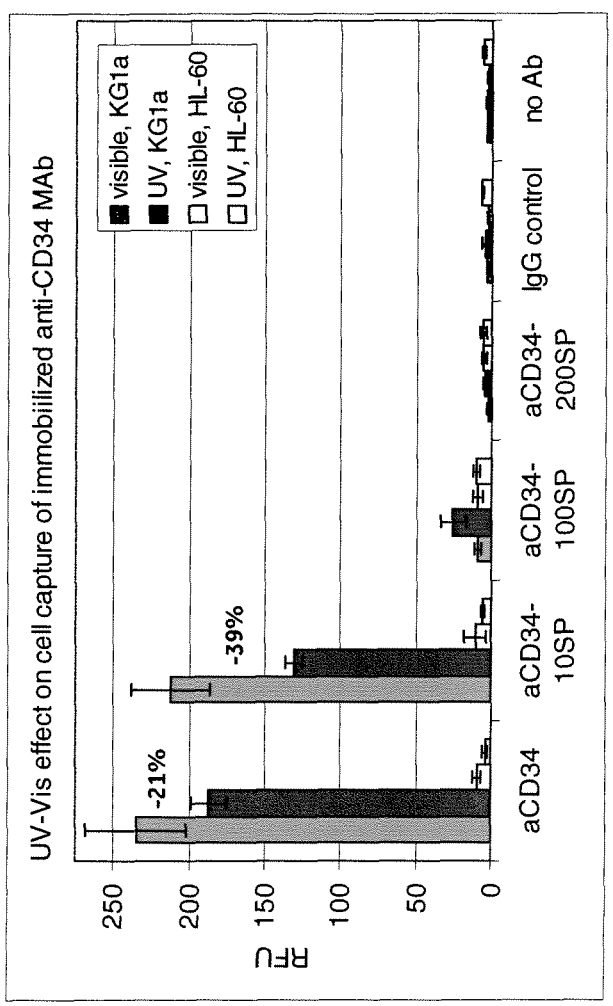
FIG. 7 is a graph of an example of the UV-Vis effect on cell capture of immobilized anti-CD34 Mab.

FIG. 7 clearly indicates enhanced release of the target KG-1a cell population following UVA exposure to αCD34-SP conjugates relative to a similar exposure to unmodified αCD34.

Example 16

Immobilized αCD34-SP Capture and UVA-Induced Release of CD34+ KG1a Cells Labeled with CellTrace Far Red CellTrace Far Red (CTFR) cell labeling, antibody immobilization, and microplate incubation and light exposure conditions were performed in a manner identical to Example 15.

Figure 8:
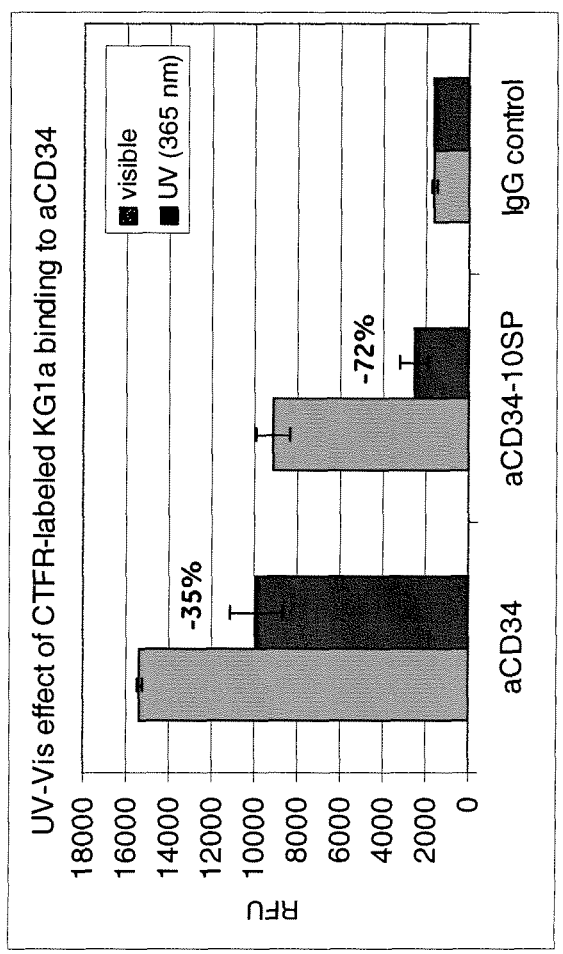
FIG. 8 is a graph of an example of the UV-Vis effect of CTGR-label KG1a binding to aCD34.

FIG. 8 demonstrates enhanced release of CTFR-labeled KG-1a upon exposure of immobilized αCD34-SP to UVA relative to what is observed for CTG-labeled cells. CTFR covalently modifies the exterior of cells and is presumed to perturb the inherent recognition of CD34 biomarker with antibody.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for binding and releasing cells, comprising, contacting one or more binders to the cells, wherein the binder comprises an environmentally-reactive molecular switch that can switch between a high affinity state, to bind the cells, to a low affinity state, to release the cells; and
introducing a trigger for the environmentally reactive molecular switch to cause the cells to bind to the binder; and
introducing another trigger for the environmentally reactive molecular switch to cause the cells to be released from the binder.

2. The method of claim 1, wherein the trigger comprises one or more of an acid, base, heat, light, magnetic field, electric field, a reducing agent, a salt or a combination thereof.

3. The method of claim 1, wherein the binder comprises one or more of an affibody, antibody, peptide, fragments of the one or more affibody, antibody, or peptide, or combinations thereof.

4. A method for binding and releasing one or more cells, comprising,
contacting one or more binders to the one or more cells, wherein the binder comprises a backbone structure and an environmentally-reactive molecular switch that can switch between a high affinity state, to bind the target, to a low affinity state, to release the target, wherein the binder is a chemically modified antibody or a fragment of a chemically modified antibody and the backbone structure is conserved; and initiating a trigger for the environmentally reactive molecular switch to cause the one or more cells to bind to the binder; and introducing another trigger for the environmentally reactive molecular switch to cause the one or more cells to be released from the binder.

5. The method of claim 4, where the one or more cells is selected from a pathogen, a virus, an antibody or antibody fragment, a protein and a nucleic acid.

6. The method of claim 4, wherein the trigger comprises one or more of an acid, base, heat, light, a reducing agent, a salt or a combination thereof.

7. The method of claim 1, further comprising a step of modifying the binder to have differing levels of sensitivity to an environmental cue.

8. The method of claim 1, further comprising a step of modifying the binder to recognize different cells while retaining sensitivity to an environmental cue.

\* \* \* \* \*

SEQUENCE LISTING

<160> NUMBER OF SEQ ID NOS: 14

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-GSGS-CS1 construct
<220> FEATURE:
<223> OTHER INFORMATION: N-term linked to biotin
<220> FEATURE:
<221> NAME/KEY: DISULFID
<222> LOCATION: (5)..(39)
<220> FEATURE:
<223> OTHER INFORMATION: C-term NH2

<400> SEQUENCE: 1

Gly Ser Gly Ser Cys Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Cys
        35

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-GSGS-CS1 construct
<220> FEATURE:
<223> OTHER INFORMATION: N-term linked to biotin

<400> SEQUENCE: 2

Gly Ser Gly Ser Cys Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Cys
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-VENK-CS2 construct
<220> FEATURE:
<223> OTHER INFORMATION: N-term linked to biotin
<220> FEATURE:
<221> NAME/KEY: DISULFID
<222> LOCATION: (5)..(39)
<220> FEATURE:
<223> OTHER INFORMATION: C-term NH2

<400> SEQUENCE: 3

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

```
<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-VENK-CS2 construct
<220> FEATURE:
<223> OTHER INFORMATION: N-term linked to biotin

<400> SEQUENCE: 4

Val Glu Asn Lys Cys Asn Lys Glu Met Arg Asn Ala Tyr Trp Glu Ile
1               5                   10                  15

Ala Leu Leu Pro Asn Leu Asn Asn Gln Gln Lys Arg Ala Phe Ile Arg
            20                  25                  30

Ser Leu Tyr Asp Asp Pro Cys
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      Cy5-VENK-CS3 construct
<220> FEATURE:
<223> OTHER INFORMATION: N-term linked to Cy5
<220> FEATURE:
<221> NAME/KEY: MOD_RES
<222> LOCATION: (5)..(5)
<223> OTHER INFORMATION: Homocysteine
<220> FEATURE:
<221> NAME/KEY: DISULFID
<222> LOCATION: (5)..(39)
<220> FEATURE:
<221> NAME/KEY: MOD_RES
<222> LOCATION: (39)..(39)
<223> OTHER INFORMATION: Homocysteine
<220> FEATURE:
<223> OTHER INFORMATION: C-term NH2

<400> SEQUENCE: 5

Val Glu Asn Lys Cys Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Cys
        35

<210> SEQ ID NO 6
<211> LENGTH: 39
<212> TYPE: PRT
<213> ORGANISM: Artificial Sequence
<220> FEATURE:
<223> OTHER INFORMATION: Description of Artificial Sequence: Synthetic
      Cy5-VENK-CS3 construct
<220> FEATURE:
<223> OTHER INFORMATION: N-term linked to Cy5
<220> FEATURE:
<221> NAME/KEY: MOD_RES
<222> LOCATION: (5)..(5)
<223> OTHER INFORMATION: Homocysteine
<220> FEATURE:
<221> NAME/KEY: MOD_RES
<222> LOCATION: (39)..(39)
<223> OTHER INFORMATION: Homocysteine

<400> SEQUENCE: 6

Val Glu Asn Lys Cys Asn Lys Glu Met Arg Asn Arg Tyr Trp Glu Ala
1               5                   10                  15
```

```
Ala Leu Asp Pro Asn Leu Asn Asn Gln Gln Lys Arg Ala Lys Ile Arg
            20                  25                  30

Ser Ile Tyr Asp Asp Pro Cys
        35

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      Cy5-VENK-CS4 construct
<220> FEATURE:
<223> OTHER INFORMATION: N-term linked to Cy5
<220> FEATURE:
<221> NAME/KEY: MOD_RES
<222> LOCATION: (5)..(5)
<223> OTHER INFORMATION: Homocysteine

<400> SEQUENCE: 7

Val Glu Asn Lys Cys Asn Lys Glu Met Arg Asn Arg Tyr Trp Glu
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      Cy5-VENK-CS4 construct

<400> SEQUENCE: 8

Ala Leu Asp Pro Asn Leu Asn Asn Gln Gln Lys Arg
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      Cy5-VENK-CS4 construct
<220> FEATURE:
<221> NAME/KEY: MOD_RES
<222> LOCATION: (10)..(10)
<223> OTHER INFORMATION: Homocysteine
<220> FEATURE:
<223> OTHER INFORMATION: C-term NH2

<400> SEQUENCE: 9

Lys Ile Arg Ser Ile Tyr Asp Asp Pro Cys
1               5                   10

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      Cy5-VENK-CS1 construct
<220> FEATURE:
<223> OTHER INFORMATION: N-term linked to Cy5
<220> FEATURE:
<221> NAME/KEY: DISULFID
<222> LOCATION: (5)..(39)
<220> FEATURE:
<223> OTHER INFORMATION: C-term NH2

<400> SEQUENCE: 10

Val Glu Asn Lys Cys Asn Lys Glu Met Arg Asn Arg Tyr Trp Glu Ala
```

```
                     1               5                  10                 15
Ala Leu Asp Pro Asn Leu Asn Asn Gln Gln Lys Arg Ala Lys Ile Arg
            20                  25                 30

Ser Ile Tyr Asp Asp Pro Cys
        35

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      Cy5-VENK-CS5 construct
<220> FEATURE:
<223> OTHER INFORMATION: N-term linked to Cy5
<220> FEATURE:
<223> OTHER INFORMATION: C-term NH2

<400> SEQUENCE: 11

Val Glu Asn Lys Phe Asn Lys Glu Met Arg Asn Arg Tyr Trp Glu Ala
1               5                  10                 15

Ala Leu Asp Pro Asn Leu Asn Asn Gln Gln Lys Arg Ala Lys Ile Arg
            20                  25                 30

Ser Ile Tyr Asp Asp Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-LC-LC-VENK-CS4 construct
<220> FEATURE:
<223> OTHER INFORMATION: N-term linked to Biotin-LC-LC
<220> FEATURE:
<221> NAME/KEY: MOD_RES
<222> LOCATION: (5)..(5)
<223> OTHER INFORMATION: Homocysteine
<220> FEATURE:
<221> NAME/KEY: MOD_RES
<222> LOCATION: (16)..(16)
<223> OTHER INFORMATION: Isobutyric acid
<220> FEATURE:
<221> NAME/KEY: MOD_RES
<222> LOCATION: (29)..(29)
<223> OTHER INFORMATION: Isobutyric acid
<220> FEATURE:
<221> NAME/KEY: MOD_RES
<222> LOCATION: (39)..(39)
<223> OTHER INFORMATION: Homocysteine
<220> FEATURE:
<223> OTHER INFORMATION: C-term NH2

<400> SEQUENCE: 12

Val Glu Asn Lys Cys Asn Lys Glu Met Arg Asn Arg Tyr Trp Glu Xaa
1               5                  10                 15

Ala Leu Asp Pro Asn Leu Asn Asn Gln Gln Lys Arg Xaa Lys Ile Arg
            20                  25                 30

Ser Ile Tyr Asp Asp Pro Cys
        35

<210> SEQ ID NO 13
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-PEG12-VENK-CS3 construct
```

```
<220> FEATURE:
<223> OTHER INFORMATION: N-term linked to Biotin-PEG12
<220> FEATURE:
<221> NAME/KEY: MOD_RES
<222> LOCATION: (5)..(5)
<223> OTHER INFORMATION: Homocysteine
<220> FEATURE:
<221> NAME/KEY: MOD_RES
<222> LOCATION: (39)..(39)
<223> OTHER INFORMATION: Homocysteine
<220> FEATURE:
<223> OTHER INFORMATION: C-term NH2

<400> SEQUENCE: 13

Val Glu Asn Lys Cys Asn Lys Glu Met Arg Asn Arg Tyr Trp Glu Ala
1               5                   10                  15

Ala Leu Asp Pro Asn Leu Asn Asn Gln Gln Lys Arg Ala Lys Ile Arg
            20                  25                  30

Ser Ile Tyr Asp Asp Pro Cys
            35

<210> SEQ ID NO 14
<211> LENGTH: 39
<212> TYPE: PRT
<213> ORGANISM: Artificial Sequence
<220> FEATURE:
<223> OTHER INFORMATION: Description of Artificial Sequence: Synthetic
      Biotin-PEG12-VENK-CS4 construct
<220> FEATURE:
<223> OTHER INFORMATION: N-term linked to Biotin-PEG12
<220> FEATURE:
<221> NAME/KEY: MOD_RES
<222> LOCATION: (5)..(5)
<223> OTHER INFORMATION: Homocysteine
<220> FEATURE:
<221> NAME/KEY: MOD_RES
<222> LOCATION: (16)..(16)
<223> OTHER INFORMATION: Isobutyric acid
<220> FEATURE:
<221> NAME/KEY: MOD_RES
<222> LOCATION: (29)..(29)
<223> OTHER INFORMATION: Isobutyric acid
<220> FEATURE:
<221> NAME/KEY: MOD_RES
<222> LOCATION: (39)..(39)
<223> OTHER INFORMATION: Homocysteine
<220> FEATURE:
<223> OTHER INFORMATION: C-term NH2

<400> SEQUENCE: 14

Val Glu Asn Lys Cys Asn Lys Glu Met Arg Asn Arg Tyr Trp Glu Xaa
1               5                   10                  15

Ala Leu Asp Pro Asn Leu Asn Asn Gln Gln Lys Arg Xaa Lys Ile Arg
            20                  25                  30

Ser Ile Tyr Asp Asp Pro Cys
            35
```